(12) United States Patent
Xie et al.

(10) Patent No.: US 11,970,727 B1
(45) Date of Patent: Apr. 30, 2024

(54) PATHOGENIC MICROORGANISM SAMPLE COLLECTION AND PRESERVATION DEVICE WITH PROTECTION FUNCTION

(71) Applicants: Yanhua Xie, North Haven, CT (US); Yansen Xie, North Haven, CT (US); Mitchell Brown, North Haven, CT (US)

(72) Inventors: Yanhua Xie, North Haven, CT (US); Yansen Xie, North Haven, CT (US); Mitchell Brown, North Haven, CT (US)

( * ) Notice: Subject to any disclaimer, the term of this patent is extended or adjusted under 35 U.S.C. 154(b) by 0 days.

(21) Appl. No.: 18/148,562

(22) Filed: Dec. 30, 2022

(51) Int. Cl.
*C12Q 1/02* (2006.01)
*B01L 3/00* (2006.01)

(52) U.S. Cl.
CPC .................. *C12Q 1/02* (2013.01); *B01L 3/50* (2013.01); *B01L 3/565* (2013.01); *B01L 2300/024* (2013.01); *B01L 2300/0609* (2013.01); *B01L 2300/0848* (2013.01); *B01L 2300/0861* (2013.01)

(58) Field of Classification Search
CPC ... C12Q 1/02; B01L 3/50; B01L 3/565; B01L 2300/024; B01L 2300/0609; B01L 2300/0848; B01L 2300/0861
USPC ...................................................... 435/307.1
See application file for complete search history.

(56) References Cited

U.S. PATENT DOCUMENTS

| | | | | |
|---|---|---|---|---|
| 4,136,680 A | * | 1/1979 | Southworth | C12M 33/02 600/572 |
| 4,353,868 A | * | 10/1982 | Joslin | C12M 33/02 435/304.2 |
| 5,320,255 A | * | 6/1994 | Stoffel | B65D 83/42 222/402.1 |
| 5,934,496 A | * | 8/1999 | Mogard | B65B 7/2878 220/837 |

* cited by examiner

*Primary Examiner* — Jill A Warden
*Assistant Examiner* — Jacqueline Brazin
(74) *Attorney, Agent, or Firm* — RC Trademark Company

(57) ABSTRACT

The present disclosure discloses a pathogenic microorganism sample collection and preservation device with a protection function, including a sampler and a preservation container; the sampler and the preservation container are both packaged by independent aseptic packaging bags. The sampler includes a sample collection mechanism, a holding mechanism, and a protection mechanism arranged between the sample collection mechanism and the holding mechanism. Before sample collection, the preservation container is sealed by an assorted sealing cover. The sample collection and preservation device of the present disclosure is convenient for holding and flexible adjustment of a sample collection angle. The protection mechanism between the holding mechanism and the sample collection mechanism plays a role of shielding, thus avoiding the problem of cross contamination. In addition, the sampler and the preservation container are matched ingeniously, so that a reliable sealing effect is achieved, which avoids spilling or contamination during sample preservation and transferring.

6 Claims, 5 Drawing Sheets

PATHOGENIC MICROORGANISM SAMPLE COLLECTION AND PRESERVATION DEVICE WITH PROTECTION FUNCTION

TECHNICAL FIELD

The present disclosure relates to a pathogenic microorganism sample collection and preservation device with a protection function, and belongs to the technical field of microorganism sample collection and detection.

BACKGROUND

Collection of pathogenic microorganism samples is an important step to detect pathogenic microorganism species, such as collection of pathogenic microorganism samples in the oral cavity, the nasal cavity, the vagina and other lesion positions.

At present, cotton swabs are mainly used for collection. In order to guarantee the sample collection accuracy and avoid harmful spreading of microorganisms, a sample collection portion of a cotton swab should not be contaminated by environmental microorganisms during sample collection, and the hands of sample collection personnel should not be contaminated by samples. However, as there is no shield between a holding position of the cotton swab and a sample collection position, cross contamination between the samples and the hands of the sample collection personnel will be caused easily. Medical staff can avoid the contamination problem due to standardized operation and adequate health protection, but they need to wear gloves and be strictly disinfected before collection at each time. The operation is cumbersome and affects the sample collection efficiency. When ordinary users collect samples at home, they are unable to achieve strict health protection due to lack of professional training. As a result, samples are easily contaminated or hands are easily contaminated by the hands.

In addition, after sample collection, the sample collection position has to be separated from the holding position, which further adds the operation complexity.

SUMMARY

The technical problem to be solved by the present disclosure is to provide a pathogenic microorganism sample collection and preservation device with a protection function, which is convenient for holding and flexible adjustment of a sample collection angle. A protection mechanism between a holding mechanism and a sample collection mechanism plays a role of shielding, thus avoiding the problem of cross contamination. In addition, a sampler and a preservation container are matched ingeniously, so that a reliable sealing effect is achieved, which avoids spilling or contamination during sample preservation and transferring.

In order to achieve the above objective, the technical solution adopted by the present disclosure is as follows: A pathogenic microorganism sample collection and preservation device with a protection function includes a sampler and a preservation container; the sampler and the preservation container are both packaged by independent aseptic packaging bags. The sampler includes a sample collection mechanism, a holding mechanism, and a protection mechanism arranged between the sample collection mechanism and the holding mechanism. Before sample collection, the preservation container is sealed by an assorted sealing cover.

Preferably, during sample collection, the protection mechanism forms a shield between the holding mechanism and the sample collection mechanism to avoid cross contamination between pathogenic microorganism samples and the holding mechanism; after the sample collection, the sealing cover of the preservation container is removed; and the sampler is hermetically connected with the preservation container through the protection mechanism to hermetically store the sample collection mechanism in the preservation container, so that the sample collection mechanism is avoided from being contaminated, and the samples are prevented from spilling.

Preferably, the sample collection mechanism includes a thief rod and a sample adsorption layer (such as bristles or medical cotton) attached to the thief rod; the protection mechanism includes a protection cover; a front surface of the protection cover is provided with an inner protection rim and an outer protection rim; a top of the preservation container is clamped between the inner protection rim and the outer protection rim in a threaded connection manner; and the holding mechanism is arranged on a back surface of the protection cover.

Preferably, threads are formed on an outer wall of the inner protection rim, an inner wall of the outer protection rim, and an inner wall and an outer wall of the top of the preservation container.

Preferably, the inner protection rim is made of an elastic material (such as rubber), and the outer protection rim is made of a hard rigid material (such as plastic).

Preferably, the inner protection rim is higher than the outer protection rim; expansion joints are uniformly arranged on the inner protection rim; the expansion joints are filled with thin films; and without an external force, the inner protection rim is flaring.

Preferably, the holding mechanism is a flip ring which is flush with an outer surface of the protection cover when being stored.

Preferably, an edge of the protection cover is flush with the outer protection rim.

Preferably, an edge of the protection cover protrudes from an outer surface of the outer protection rim to form a protection flange; release paper is stuck on the outer surface of the protection flange; and an absorption layer is laid on a surface layer of the release paper.

The above technical solution achieves the following beneficial effects: The sample collection and preservation device of the present disclosure is convenient for holding and flexible adjustment of a sample collection angle. The protection mechanism between the holding mechanism and the sample collection mechanism plays a role of shielding, thus avoiding the problem of cross contamination. In addition, the sampler and the preservation container are matched ingeniously, so that a reliable sealing effect is achieved, which avoids spilling or contamination during sample preservation and transferring.

BRIEF DESCRIPTION OF THE DRAWINGS

The present disclosure is further described in detail below in combination with accompanying drawings and specific implementations.

Figure 1:
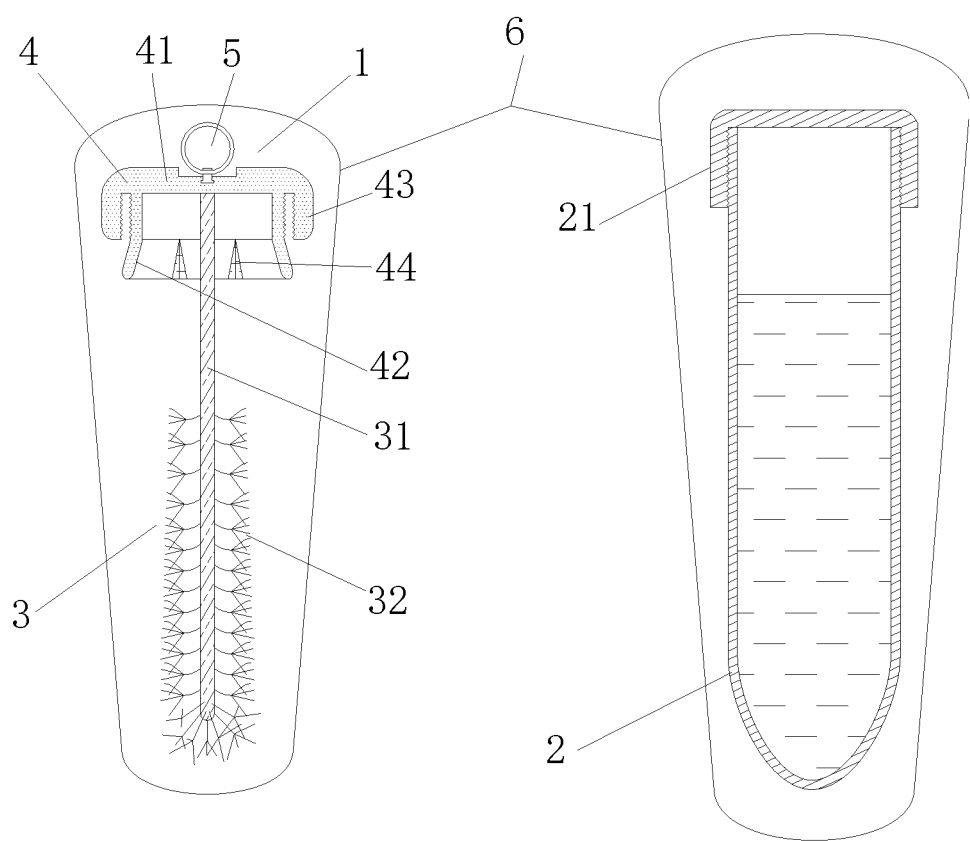
FIG. 1 is an assembly relationship diagram of a sampler and a preservation container before sample collection.
Figure 2:
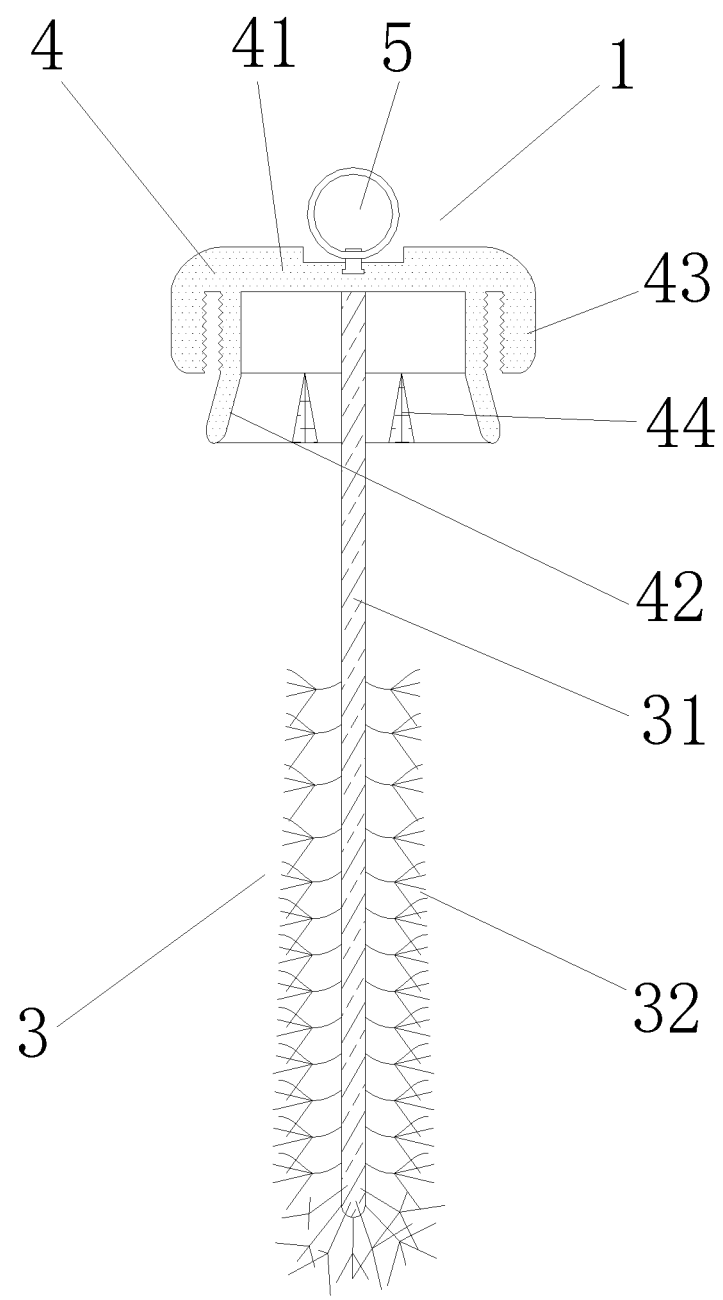
FIG. 2 is a usage state diagram of taking the sampler from the preservation container for sample collection.
Figure 3:
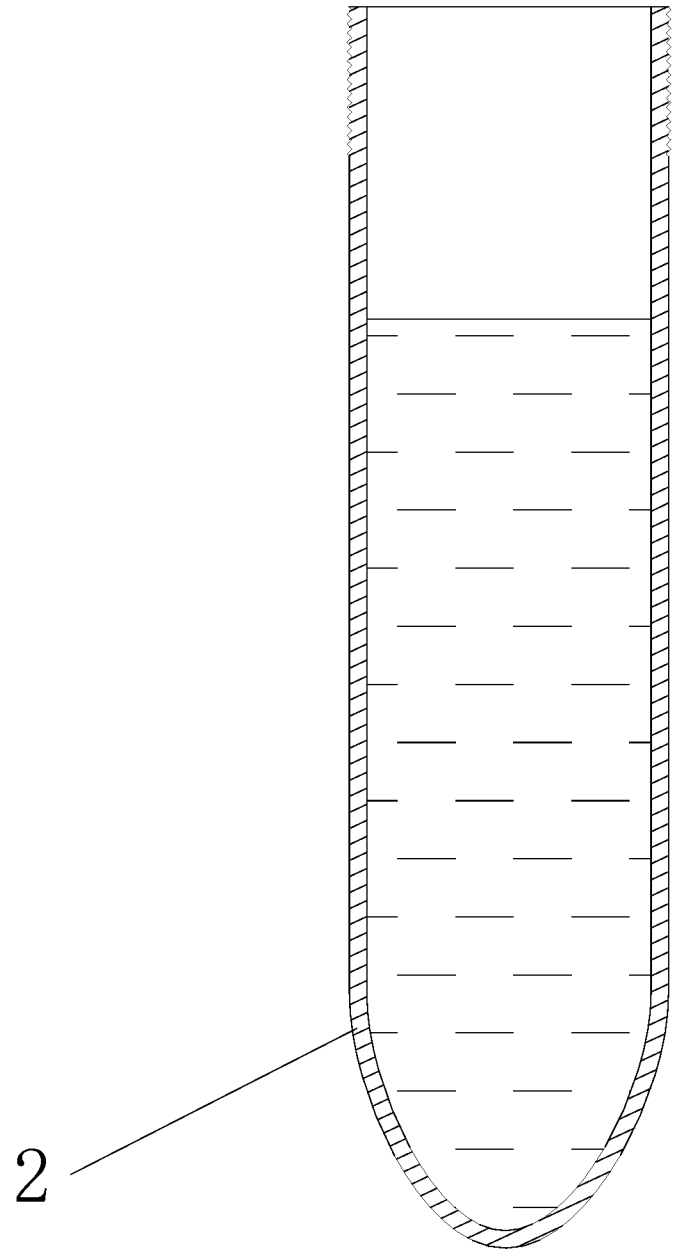
FIG. 3 is a schematic diagram of removing a sealing cover from the preservation container.
Figure 4:
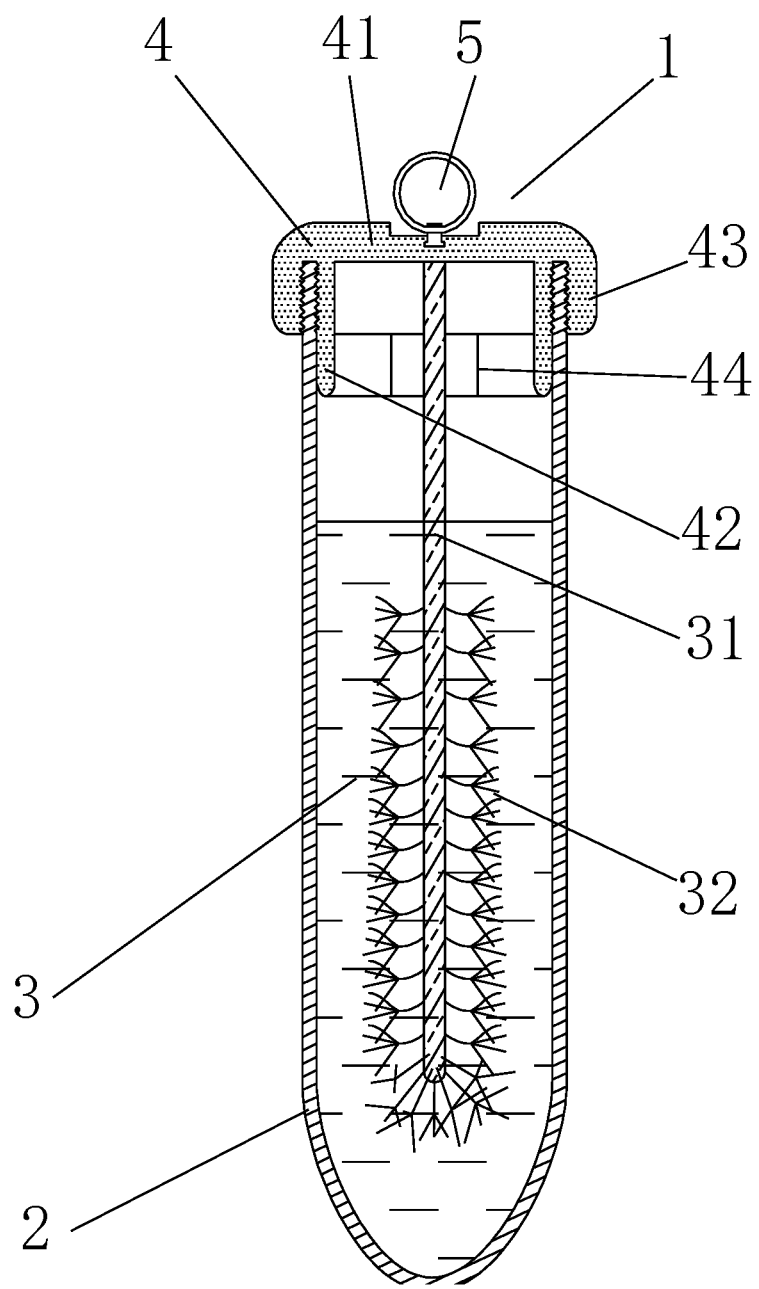
FIG. 4 is a schematic diagram of putting the sampler into the preservation container for sealing and preservation after sample collection.

In the drawings: 1: sampler; 2: preservation container; 3: sample collection mechanism; 4: protection mechanism; 5: holding mechanism; 6: aseptic packaging bag; 21: sealing cover; 31: thief rod; 32: sample adsorption layer; 41: protection cover; 42: inner protection rim; 43: outer protection rim; 44: expansion joint; 45: thin film; 46: protection flange; and 47: release paper.

DETAILED DESCRIPTION OF THE EMBODIMENTS

Referring to FIG. 1 to FIG. 5 at the same time, the structure of a pathogenic microorganism sample collection and preservation device includes a sampler 1 and a preservation container 2. The sampler 1 and the preservation container 2 are both packaged by independent aseptic packaging bags 6. The sampler 1 includes a sample collection mechanism 3, a holding mechanism 5, and a protection mechanism 4 arranged between the sample collection mechanism 3 and the holding mechanism 5. Before sample collection, the preservation container 2 is sealed by an assorted sealing cover 21.

Preferably, during sample collection, the protection mechanism 4 forms a shield between the holding mechanism 5 and the sample collection mechanism 3 to avoid cross contamination between pathogenic microorganism samples and the holding mechanism 5. After the sample collection, the sealing cover 21 of the preservation container 2 is removed. The sampler 1 is hermetically connected with the preservation container 2 through the protection mechanism 4 to hermetically store the sample collection mechanism 3 in the preservation container 2, so that the sample collection mechanism 3 is avoided from being contaminated, and the samples are prevented from spilling.

The sample collection mechanism 3 includes a thief rod 31 and a sample adsorption layer 32 (such as bristles or medical cotton) attached to the thief rod 31. The protection mechanism 4 includes a protection cover 41. A front surface of the protection cover 41 is provided with an inner protection rim 42 and an outer protection rim 43. A top of the preservation container 2 is clamped between the inner protection rim 42 and the outer protection rim 43 in a threaded connection manner.

The holding mechanism 5 is arranged on a back surface of the protection cover 41. The sample adsorption layer 32 is used for adsorbing a sample with pathogenic microorganisms. The protection mechanism 4 can avoid the holding mechanism 5 and the hands of sample collection personnel from being contaminated by the sample during the sample collection. The protection mechanism 4 will block the sample even if the sample flows along the thief rod 31. For sample preservation, there are two layers of seals, i.e. the inner protection rim 42 and the outer protection rim 43, the sealing property for sample preservation is guaranteed.

Threads are formed on an outer wall of the inner protection rim 42, an inner wall of the outer protection rim 43, and an inner wall and an outer wall of the top of the preservation container 2. By means of threaded connection, the product is quickly assembled and disassembled, high in reliability, and convenient to manufacture.

The inner protection rim 42 is made of an elastic material (such as rubber), and the outer protection rim 43 is made of a hard rigid material (such as plastic). The inner protection rim 42 is elastic, which further enhances the first layer of sealing shield. The outer protection rim 43 is highly rigid, which can improve the stability of threaded connection.

The inner protection rim 42 is higher than the outer protection rim 43. The inner protection rim 42 is a first layer of anti-contamination shield between the sample and the holding mechanism 5 and is also a component that mainly achieves a sealing effect for preservation. The inner protection rim 42 is higher, which can lower the protection risk of the outer protection rim 43. Expansion joints 44 are uniformly arranged on the inner protection rim 42. The expansion joints 44 are filled with thin films 45. Without an external force, the inner protection rim 42 is flaring. During the sample collection, the inner protection rim 42 opens up, which enlarges the protection range. During sealing, the inner protection rim 42 tends to open up outwards to make the outer wall of the inner protection rim 42 closely fitted to the inner wall of the preservation container 2, which further improves the sealing property.

The holding mechanism 5 can be a flip ring, which is flexible to hold and convenient for adjusting a sample collection angle. In a stored state, the holding mechanism 5 is flush with an outer surface of the protection cover 41, so that the probability that the holding mechanism 5 is pulled by an external force can be avoided during transferring and preservation.

In one embodiment shown in FIG. 1 to FIG. 4, an edge of the protection cover 41 in this embodiment is flush with the outer protection rim 43. This embodiment is applicable to a small sample distribution range.

Figure 5:
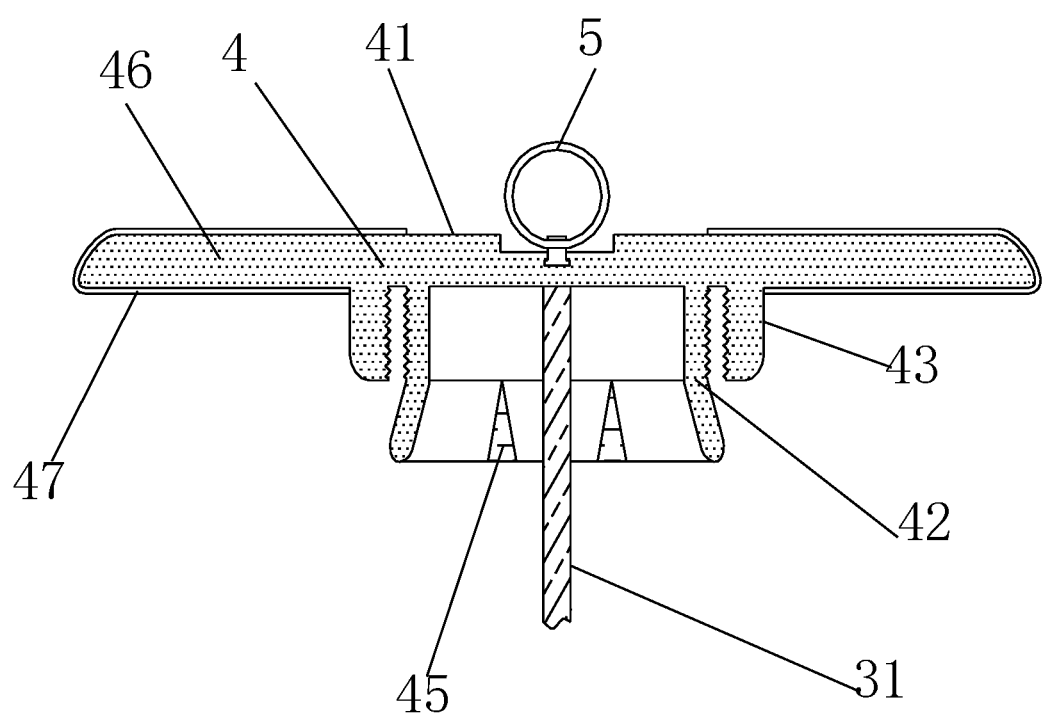
FIG. 5 is a structural diagram of an embodiment where an edge of a protection cover protrudes from an outer surface of an outer protection rim.

In one embodiment shown in FIG. 5 alone, an edge of the protection cover 41 in this embodiment protrudes from an outer surface of the outer protection rim 43 to form a protection flange 46. Release paper 47 is stuck on the outer surface of the protection flange 46. An absorption layer is laid on a surface layer of the release paper 47. This embodiment is applicable to a large sample distribution range, that is, which is beyond the outer protection rim 43. When a sample of a certain position is collected, there is still a risk nearby of contaminating the holding mechanism 5. The protection range is enlarged by means of the protection flange 46. When the protection flange 46 is contaminated, the release paper 47 is torn away to eliminate disturbance terms and keep the protection flange 46 clean.

The above description is only proposed as an implementable technical solution of the present disclosure and is not a single restriction condition for the technical solution.

What is claimed is:

1. A pathogenic microorganism sample collection and preservation device with a protection function, comprising a sampler and a preservation container, wherein the sampler and the preservation container are both packaged by independent aseptic packaging bags; the sampler includes a sample collection mechanism, a holding mechanism, and a protection mechanism arranged between the sample collection mechanism and the holding mechanism; and before sample collection, the preservation container is sealed by a sealing cover wherein during sample collection, the protection mechanism is disposed between the holding mechanism and the sample collection mechanism to avoid cross contamination between pathogenic microorganism samples and the holding mechanism, after the sample collection, the sealing cover of the preservation container is removed, and the sampler is hermetically connected with the preservation container through the protection mechanism to hermetically store the sample collection mechanism in the preservation container, so that the sample collection mechanism is avoided from being contaminated, and the samples are prevented from spilling, wherein the sample collection mechanism comprises a thief rod a sample adsorption layer attached to the thief rod, the protection mechanism comprises a protection cover; a front surface of the protection cover is provided with an inner protection rim and an outer protection rim, a top of the preservation container is clamped between the inner protection rim and the outer protection rim in a threaded connection manner; and the holding mechanism is arranged on a back surface of the protection cover wherein expansion joints are uniformly arranged on the inner protection rim, the expansion joints are filled with thin films; and without an external force, the inner protection rim is flaring.

2. The pathogenic microorganism sample collection and preservation device with the protection function according to claim 1, wherein threads are formed on an outer wall of the inner protection rim, an inner wall of the outer protection rim, and an inner wall and an outer wall of the top of the preservation container.

3. The pathogenic microorganism sample collection and preservation device with the protection function according to claim 1, wherein the inner protection rim is made of an elastic material, and the outer protection rim is made of a hard rigid material (such as plastic).

4. The pathogenic microorganism sample collection and preservation device with the protection function according to claim 1, wherein the holding mechanism is a flip ring which is flush with an outer surface of the protection cover when being stored.

5. The pathogenic microorganism sample collection and preservation device with the protection function according to claim 1, wherein an edge of the protection cover is flush with the outer protection rim.

6. The pathogenic microorganism sample collection and preservation device with the protection function according to claim 1, wherein an edge of the protection cover protrudes from an outer surface of the outer protection rim to form a protection flange; release paper is stuck on the outer surface of the protection flange; and an absorption layer is laid on a surface layer of the release paper.

* * * * *